US00PP30954P2

(12) United States Plant Patent
Scheiber

(10) Patent No.: US PP30,954 P2
(45) Date of Patent: Oct. 22, 2019

(54) ***ABELIA* PLANT NAMED 'SRPABEPER'**

(50) Latin Name: ***Abelia* hybrid**
Varietal Denomination: SRPabeper

(71) Applicant: THE CONARD-PYLE COMPANY, West Grove, PA (US)

(72) Inventor: Sloane Scheiber, West Grove, PA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,719

(22) Filed: Apr. 13, 2018

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP16,988 P2 8/2006 Lindsey
PP20,961 P2 4/2010 Van Opstal

*Primary Examiner* — Susan McCormick Ewoldt
(74) *Attorney, Agent, or Firm* — Buchanan Ingersoll & Rooney PC

(57) ABSTRACT

A new and distinct variety of *Abelia* plant, herein referred to by its cultivar name, 'SRPabeper', is provided which forms on a substantially continuous basis attractive white colored flowers. Attractive, tri-colored orange, yellow, and green colored foliage is formed. The growth habit is moderately vigorous and compact and well-branched. The new variety is well suited for providing attractive ornamentation in the landscape.

3 Drawing Sheets

Figure 1:
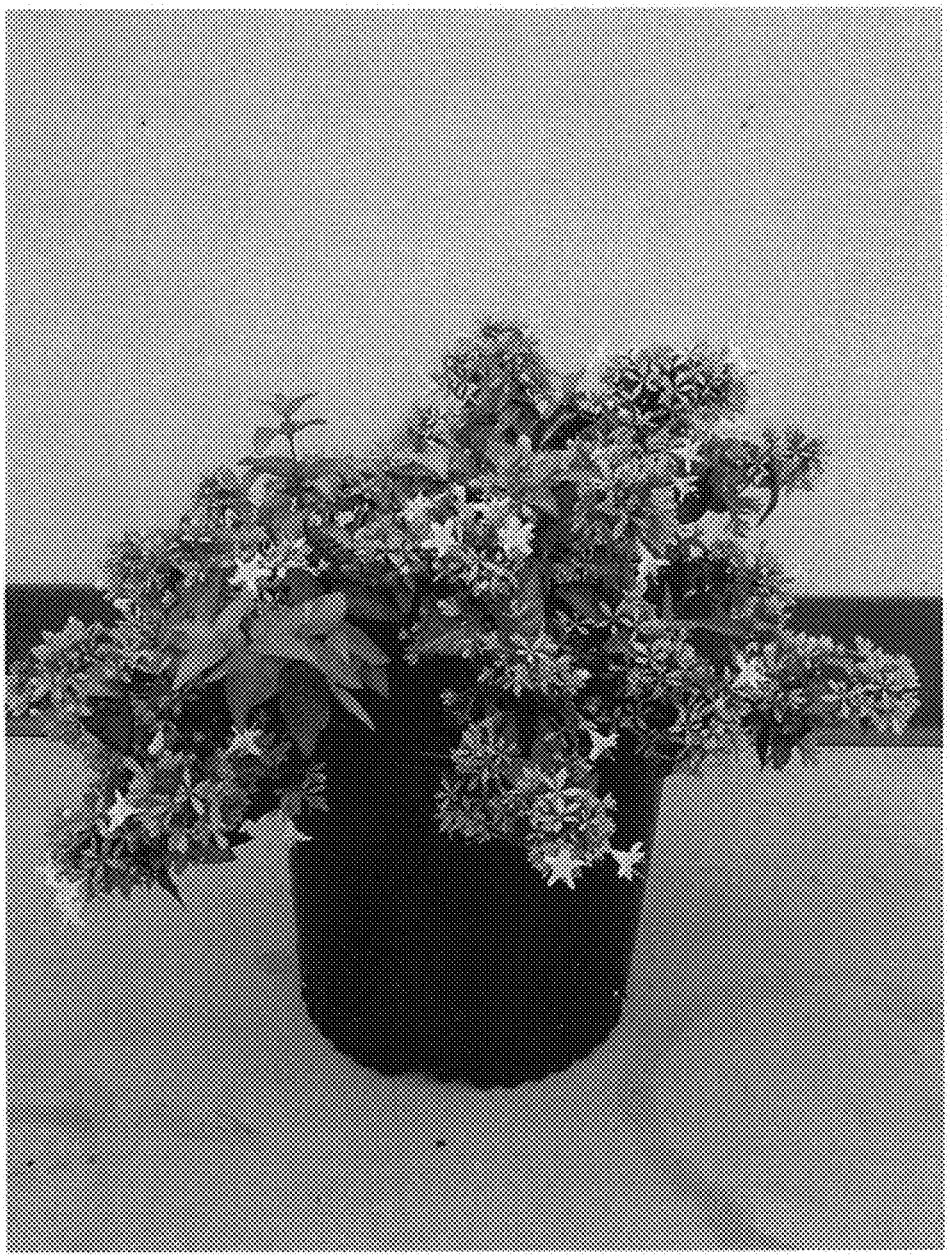

Botanical/commercial classification:
Latin name—*Abelia* hybrid.
Varietal denomination—'SRPabeper'.

SUMMARY OF THE INVENTION

The new variety of *Abelia hybrida* plant originated in a controlled breeding program in West Grove, Pa. during June, 2010. The objective of the breeding program was the development of *Abelia* cultivars with large flowers, attractive foliage coloration, and improved hardiness. The new cultivar was created by cross-pollination wherein two parents were crossed which previously had been studied in the hope that they would contribute the desired characteristics. The female parent (i.e., the seed parent) was the *Abelia chinensis* (non-patented in the United States). The male parent (i.e., the pollen parent) was the *Abelia* x *grandiflora* 'Kaleidoscope' variety (U.S. Plant Pat. No. 16,988).

The parentage of the new variety can be summarized as follows:

*Abelia chinensis* x 'Kaleidoscope'

The new cultivar was discovered and selected as a single flowering plant from the progeny resulting from the above pollination during September, 2013 in a controlled environment in West Grove, Pa. Selective study resulted in the identification of a single plant of the new variety.

It was found that the new variety of *Abelia* plant of the present invention:

(a) substantially continuously forms white colored flowers,
(b) displays tri-colored foliage colored orange, yellow, and green, (c) exhibits a moderately vigorous and compact and well-branched growth habit, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the *Abelia chinensis* variety (i.e., the seed parent) displays medium green colored foliage and an upright to rounded growth habit, while the new variety provides tri-colored foliage colored orange, yellow, and green and displays compact and well-branched growth habit. The 'Kaleidoscope' variety (i.e., the pollen parent) displays dark and light yellow-green variegated foliage and a spreading to broadly upright growth habit, while the new variety provides tri-colored foliage colored orange, yellow, and green and displays compact and well-branched growth habit.

The new variety can also be distinguished from other similar varieties that are commercially available. For instance, the new variety of the present invention can readily be distinguished from the 'Abelops' variety (U.S. Plant Pat. No. 20,961), as the new cultivar displays a more compact growth habit than the 'Abelops' variety and the foliage of the new variety is orange, yellow, and green tri-colored, whereas the 'Abelops' variety displays dark and light yellow-green variegated foliage edge.

The new variety has been found to undergo asexual reproduction by a number of routes, including terminal stem cuttings. Asexual propagation by the above-mentioned techniques in West Grove, Pa. since September 2013 has shown that the characteristics of the new variety are stable and are strictly transmissible by such asexual propagation from one generation to another. Accordingly, the new variety undergoes asexual propagation in a true-to-type manner.

The new variety has been named 'SRPabeper'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'SRPabeper' variety. The plants were grown in one-gallon pots for approximately five months outside at West Grove, Pa. Plants were pinched once after transplant.

FIG. 1—illustrates a specimen of the plant displaying the overall growth and flowering habit—side view.

Figure 2:
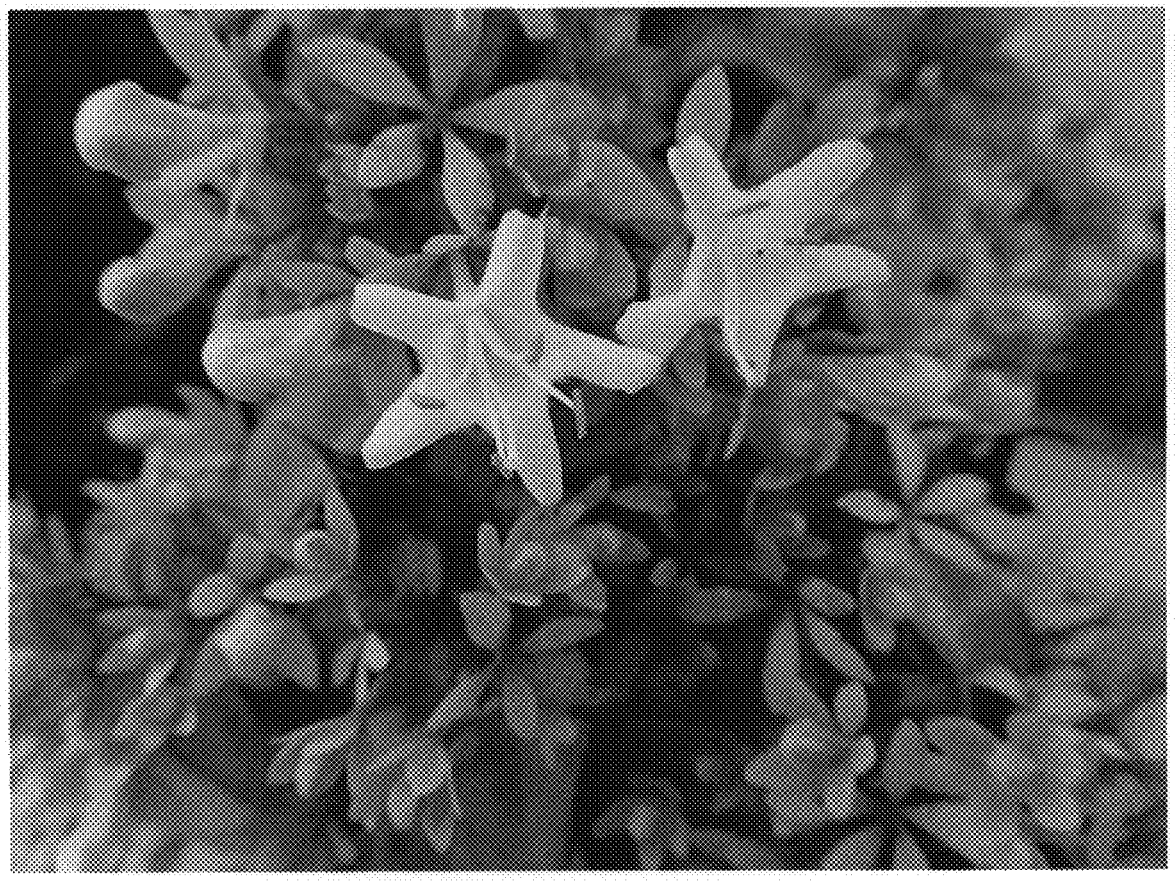

FIG. 2—illustrates a specimen of an inflorescence in the course of opening.

Figure 3:
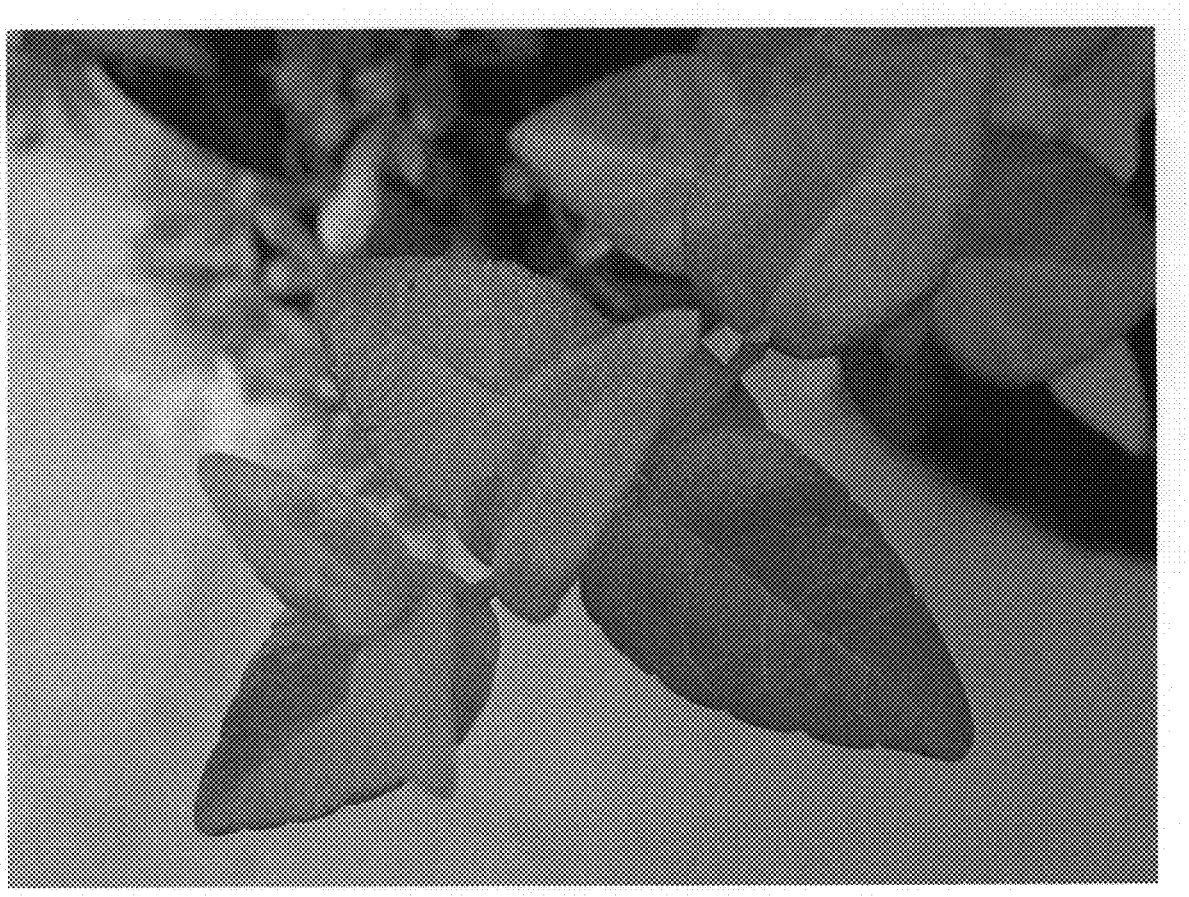

FIG. 3—illustrates a specimen of leaves—plan view—obverse.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in September 2017 under natural light conditions in West Grove, Pa. The description is based on the observation of plants produced from cuttings from stock plants and grown in one-gallon containers for approximately five months in an outdoor nursery in West Grove, Pa. Plants were pinched once after transplant.

Class: *Abelia* Plant.

Propagation:

*Type cutting*.—Terminal stem.

*Time to initiate roots*.—Approximately 10 to 14 days on average.

*Time to produce a rooted cutting*.—Approximately 21 to 25 days on average.

*Root description*.—Fibrous.

*Rooting habit*.—Freely branching.

Plant:

*Deciduous*.—Different fall colors are observed.

*Habit*.—Moderate growth vigor and compact and well-branched growth habit.

*Commercial crop time*.—Approximately 13 weeks from a rooted cutting to finish in a 1 gallon container.

*Size*.—Approximately 17.0 cm in height from soil level to top of plant plane on average; and approximately 37.0 cm in width on average.

Branches:

*Branching habit*.—Freely branching, pinching enhances basal branching.

*Quantity of main branches per plant*.—Approximately 3 on average.

*Strength*.—Commonly strong, somewhat flexible and becomes woody with age.

*Size*.—Length: approximately 16.0 cm on average. Diameter: approximately 3.0 mm on average. Length of central internode: approximately 1.0 cm on average.

*Texture*.—Viscid, densely glandular pubescent.

*Color*.—Young stems: commonly near Greyed-Orange Group N167C. Mature stems: commonly near Grey-Brown Group 199C with some outer exfoliating layers near Greyed-Orange Group 177C.

Foliage:

*Number of leaves*.—Approximately 24 per unbranched lateral stem on average; and approximately 192 per branched lateral stem on average.

*Form*.—Simple.

*Arrangement*.—Opposite.

*Durability to stress*.—Moderate to high.

Leaves:

*Shape*.—General: ovate. Margin: partially serrate. Apex: acute. Base: rounded.

*Venation pattern*.—Pinnate.

*Size*.—Length of mature leaf: approximately 2.5 cm on average. Width of mature leaf: approximately 1.0 cm on average.

*Texture*.—Upper and lower surfaces: smooth, glabrous, glossy.

*Non-fall color*.—Upper surface of young foliage: commonly near Greyed-Orange Group N170A. Lower surface of young foliage: commonly near Greyed-Yellow Group 162A. Upper surface of mature foliage: commonly near Green Group 137B with some leaves transitioning to near Yellow-Green Group 151B and near Greyed-Orange Group 167B towards the apex. Lower surface of mature foliage: commonly near Green Group 143C with a blend of near Yellow-Green Group 151A. Vein color: indistinguishable.

*Petiole*.—Shape: rounded, slightly curved. Length: approximately 1.5 mm on average. Width: approximately 1.0 mm on average. Color: commonly near Greyed-Red Group 178B.

Inflorescence:

*Quantity*.—Approximately 2 flowers per lateral stem, and approximately 16 flowers and buds per inflorescence on average.

*Type*.—Terminal compound cymes, self-cleaning with a persistent calyx.

*Fragrance*.—Very faint.

*Depth or height*.—Approximately 3.0 cm on average.

*Width*.—Approximately 3.5 cm on average.

*Rate of flower opening*.—Approximately 2 at a time per lateral branch.

*Peduncle*.—Strength: strong. Aspect: erect with secondary peduncles at an average angle of 40 degree. Length: approximately 1.2 cm on average. Diameter: approximately 1.0 mm on average. Texture: smooth, glabrous. Color: commonly near Yellow-Green Group 146C to near Greyed-Orange Group 166B on upper side which receives sunlight.

Flower:

*Type*.—Single, campanulate.

*Aspect*.—Outward to slightly drooping.

*Bud*.—Shape: obovate, curved downward. Length: approximately 1.2 cm on average. Diameter: approximately 4.0 mm on average. Color of petals: commonly near Greyed-Yellow Group 160C with a blend of near Greyed-Red Group 179D at the apex. Quantity: approximately 14 per lateral stem. Rate of opening: approximately 3 days.

*Corolla*.—Depth: approximately 2.0 cm on average. Width: approximately 1.5 cm on average.

*Petals*.—Quantity: commonly 5, fused into an irregular campanulate shape. Appearance: slightly glossy. Shape: narrow oblong. Margin: entire. Apex: obtuse. Length: approximately 1.7 cm on average. Width of upper two petals: approximately 4.0 mm on average. Width of three lower petals: approximately 5.0 mm on average. Texture of upper and lower surfaces: smooth. Color of upper surface when first and fully open: commonly near White Group NN155C with a blend of near Greyed-Purple Group 186D. Color of lower surface when first and fully open: commonly near White Group NN155C with some slight blending of near Greyed-Purple Group 186D.

*Calyx*.—Shape: rotate. Length: approximately 7.0 mm on average. Diameter: approximately 1.5 cm on average.

*Sepals*.—Quantity per flower: commonly 5 on average. Length: approximately 9.0 mm on average. Width: approximately 3.0 mm on average. Apex: acute. Margin: entire. Base: cuneate. Shape: oblanceolate. Arrangement: rotate. Appearance: slightly glossy. Texture of upper and lower surfaces: smooth. Color of immature sepals: upper surface commonly near Yellow-Green Group 144C and lower surface commonly near Yellow-Green Group 144D. Color of mature sepals: upper surface commonly near Greyed-Red Group 179C and lower surfaces commonly near Greyed-Red Group 179D with blend of near Greyed-Red Group 181B toward the apex.

*Pedicles*.—Strength: strong. Aspect: erect with secondary pedicels at an average angle of 40 degree. Length: approximately 3.0 mm on average. Width: approximately 0.5 mm on average. Texture: smooth, glabrous. Color: commonly near Yellow-Green Group 144B, upper surface tinged with near Greyed-Red Group 182A.

*Reproductive organs*.—Androecium: Stamen: commonly 4 per flower. Anther: shape is narrow oblong, versatile; length is approximately 2.0 mm on average; and coloration is commonly near Greyed-Orange Group 164D. Filament: length is approximately 1.5 cm on average and coloration is commonly near White Group N155C. Pollen: amount is moderate and coloration is commonly near White Group NN155C. Gynoecium: Pistil: commonly 1 per flower and length is approximately 1.9 cm on average. Stigma: shape is club and coloration is commonly near White Group N155A. Style: length is approximately 1.85 cm on average and coloration is commonly near White Group N155B. Ovary: coloration is commonly near Yellow-Green Group 146C. Seed and fruit: none have been observed to date.

Development:

*Blooming*.—Freely flowering under outdoor growing conditions with substantially continuous blooming from summer through autumn.

*Lastingness of individual flower*.—Approximately 5 days on average.

*Tolerance to disease*.—Not available.

The new 'SRPabeper' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Abelia* plant characterized by the following combination of characteristics:

(a) substantially continuously forms white colored flowers, (b) displays tri-colored foliage colored orange, yellow, and green, (c) exhibits a moderately vigorous and compact and well-branched growth habit, and (d) is well suited for providing attractive ornamentation; substantially as herein shown and described.

* * * * *